United States Patent
Porada et al.

(10) Patent No.: US 11,826,757 B2
(45) Date of Patent: Nov. 28, 2023

(54) NICHES-ON-A-CHIP

(71) Applicant: Wake Forest University Health Sciences, Winston-Salem, NC (US)

(72) Inventors: Christopher Daniel Porada, Winston-Salem, NC (US); Aleksander Skardal, Clemmons, NC (US); Maria Graca Almeida-Porada, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 89 days.

(21) Appl. No.: 16/635,703

(22) PCT Filed: Aug. 1, 2018

(86) PCT No.: PCT/US2018/044791
§ 371 (c)(1),
(2) Date: Jan. 31, 2020

(87) PCT Pub. No.: WO2019/028131
PCT Pub. Date: Feb. 7, 2019

(65) Prior Publication Data
US 2020/0376489 A1 Dec. 3, 2020

Related U.S. Application Data

(60) Provisional application No. 62/571,988, filed on Oct. 13, 2017, provisional application No. 62/540,391, filed on Aug. 2, 2017.

(51) Int. Cl.
*C12M 3/06* (2006.01)
*B01L 3/00* (2006.01)
(Continued)

(52) U.S. Cl.
CPC ... *B01L 3/502753* (2013.01); *B01L 3/502715* (2013.01); *C12M 21/08* (2013.01);
(Continued)

(58) Field of Classification Search
CPC ..................................................... C12M 23/16
See application file for complete search history.

(56) References Cited

U.S. PATENT DOCUMENTS 7,051,654 B2  5/2006 Boland et al.
8,691,279 B2  4/2014 Guillen et al.
(Continued)

FOREIGN PATENT DOCUMENTS

WO  2016/064648  4/2016
WO  2017/059173  4/2017

OTHER PUBLICATIONS

Choi et al., Engineering the hematopoietic stem cell niche: Frontiers in biomaterial science:, 2015, Biotechnol. J., 10, pp. 1529-1545 (Year: 2015).*
(Continued)

*Primary Examiner* — Jonathan M Hurst
(74) *Attorney, Agent, or Firm* — Myers Bigel, P.A.

(57) ABSTRACT

Provided herein according to some embodiments is an in vitro construct useful as a model for a hematopoietic microenvironment, which may include: a microfluidic device having multiple chambers; and two or more populations of cells (e.g., 3 or 4 populations of cells) (or "niches") selected from: 1) mesenchymal cells (e.g., Stro-1+; MSC); 2) osteoblasts (OB; optionally said osteoblasts provided by differentiating mesenchymal cells to differentiated osteoblasts); 3) arterial endothelium (e.g., CD146+NG2+; AEC); and 4) sinusoidal endothelium (CD146+NG2-; SEC), wherein each of said two or more populations of cells are provided in a separate chamber of the microfluidic device.

(Continued)

Methods of making and using the construct are also provided.

35 Claims, 9 Drawing Sheets

(51) Int. Cl.
  *C12M 3/00* (2006.01)
  *C12M 1/00* (2006.01)

(52) U.S. Cl.
  CPC ............ *C12M 23/16* (2013.01); *C12M 27/18* (2013.01); *B01L 2200/10* (2013.01); *B01L 2300/0861* (2013.01)

(56) References Cited

U.S. PATENT DOCUMENTS

| | | |
|---|---|---|
| 8,754,564 B2 | 6/2014 | Bennett et al. |
| 8,808,730 B2 | 8/2014 | Ratcliffe |
| 8,815,277 B2 | 8/2014 | Park et al. |
| 9,267,938 B2 | 2/2016 | Lee et al. |
| 2004/0142411 A1* | 7/2004 | Kirk ................. B82Y 30/00 435/33 |
| 2007/0243572 A1* | 10/2007 | Keymer ............. C12M 23/34 435/29 |
| 2009/0208466 A1 | 8/2009 | Yoo et al. |
| 2011/0086382 A1* | 4/2011 | Marx ................. C12M 23/16 435/325 |
| 2011/0207166 A1* | 8/2011 | Vaiselbuh ........... C12N 5/0647 435/32 |
| 2011/0250585 A1* | 10/2011 | Ingber ............... C12N 5/0623 435/5 |
| 2012/0089238 A1 | 4/2012 | Kang et al. |
| 2016/0040120 A1 | 2/2016 | Gottwald et al. |
| 2016/0137986 A1 | 5/2016 | Lee et al. |
| 2016/0313306 A1 | 10/2016 | Ingber et al. |
| 2016/0326477 A1 | 11/2016 | Fernandez-Alcon et al. |

OTHER PUBLICATIONS

Aleman et al. "Deconstructed Microfluidic Bone Marrow On-A-Chip to Study Normal and Malignant Hemopoietic Cell-Niche Interactions" Small, 15(43):1902971 (2019) (13 pp).

Aleman et al. "Supporting Information: Deconstructed Microfluidic Bone Marrow On-A-Chip to Study Normal and Malignant Hemopoietic Cell-Niche Interactions" Small, 15(43):1902971 (2019) (9 pp).

Bhise et al. "A liver-on-a-chip platform with bioprinted hepatic spheroids" Biofabrication, 8(1):014101 (2016) (12 pp).

Choi et al. "Engineering the hematopoietic stem cell niche: Frontiers in biomaterial science" Biotechnology Journal, 10(10):1529-1545 (2015). Abstract.

Cosson et al. "Ultra-rapid prototyping of flexible, multi-layered microfluidic devices via razor writing" Lab Chip, 15(1):72-76 (2015).

International Search Report and Written Opinion corresponding to PCT/US2018/044791, dated Feb. 7, 2019 (7 pp).

Kang et al. "Novel PDMS cylindrical channels that generate coaxial flow, and application to fabrication of microfibers and particles" Lab on a Chip, 10(14):1856-1861 (2010).

Mokhtari et al. "A human bone marrow mesodermal-derived cell population with hemogenic potential" Leukemia, 32:1575-1586 (2018).

Skardal et al. "A hydrogel bioink toolkit for mimicking native tissue biochemical and mechanical properties in bioprinted tissue constructs" Acta Biomaterialia, 25:24-34 (2015).

Skardal et al. "In situ patterned micro 3D liver constructs for parallel toxicology testing in a fluidic device" Biofabrication, 7(3):031001 (2015) (16 pp).

Skardal et al. "Organoid-on-a-chip and body-on-a-chip systems for drug screening and disease modeling" Drug Discovery Today, 21(9):1399-1411 (2016).

Skardal et al. "A reductionist metastasis-on-a-chip platform for in vitro tumor progression modeling and drug screening" Biotechnology and Bioengineering, 113(9):2020-2032 (2016).

Temiz et al. "Lab-on-a-chip devices: How to close and plug the lab?" Microelectronic Engineering, 132:156-175 (2015).

Zhang et al. "Multisensor-integrated organs-on-chips platform for automated and continual in situ monitoring of organoid behaviors" PNAS Plus, 114(12):E2293-E2302 (2017).

Wikipedia, "Rigid body", Retrieved from: https://en.wikipedia.org/wiki/Rigid_body#cite_note-2 on Dec. 30, 2022, 1 page.

Gordon, Emma, et al., "The Importance of Mechanical Forces for in vitro Endothelial Cell Biology", Frontiers in Physiology. 11:684 (Jun. 2020).

Ruina, Andy, et al., "Introduction to Statics and Dynamics", Oxford University Press, Chapter 1, p. 3. Retrieved from http://ruina.tam.cornell.edu/Book/ on Dec. 30, 2022 (2002).

Yourek, Gregory, et al., "Shear stress induces osteogenic differentiation of human mesenchymal stem cells", Regen Med. 5(5): 713-724 (Sep. 2010).

* cited by examiner

NICHES-ON-A-CHIP

CROSS REFERENCE TO RELATED APPLICATIONS

This application is a 35 U.S.C. § 371 national phase application of International Application Serial No. PCT/US2018/044791, filed Aug. 1, 2018, which claims the benefit of U.S. provisional patent application ser. Nos. 62/540,391 and 62/571,988, filed Aug. 2, 2017 and Oct. 13, 2017, respectively, the disclosure of which is incorporated by reference herein in its entirety.

BACKGROUND

Under normal conditions, hematopoietic stem/progenitor cells (HSPC) reside within specific bone marrow (BM) niches. These are comprised of an array of different cell types located strategically to provide myriad chemical signals and physical interactions that maintain HSC and orchestrate the process of hematopoiesis. In human myeloid malignancies, the BM niche is remodeled by malignant cells, which displace resident HSPC, and create self-reinforcing malignant niches that drive disease progression, chemoresistance, and relapse.

Attaining a mechanistic understanding of the major determinants of HSPC function in the human BM has been difficult, due to challenges associated with visualizing and modeling of the complex niche environment in humans.

To date, the vast majority of studies defining the myriad interactions that occur between normal and malignant HSPC and the niches within the BM have been performed in vivo in the murine system, given its ease of genetic manipulation and the ability to conduct in vivo imaging.

U.S. Patent Application Publication No. 2011/0207166 of Vaiselbuh is directed to an in vitro cultured permissive niche, or human bone marrow microenvironment, comprising a scaffold coated with human mesenchymal stem cells and a culture medium.

U.S. Pat. No. 9,267,938 to Lee et al. is directed to an ex vivo dynamic multiple myeloma cancer niche contained in a microfluidic device, including a bone marrow niche comprising osteoblasts, and human myeloma cells in contact with the osteoblasts.

U.S. Patent Application Publication No. 2016/0040120 of Gottwald et al. is directed to a three-dimensional model of a HSPC niche that comprises the co-culture of human HSPC and human mesenchymal stromal cells in a defined 3D environment.

However, new models to recreate the biological/functional complexity of the human BM niche are needed.

SUMMARY

Provided herein according to some embodiments is an in vitro construct useful as a model for a hematopoietic microenvironment, which may include: a microfluidic device having multiple chambers; and two or more populations of cells (e.g., 3 or 4 populations of cells) (or "niches") selected from: 1) mesenchymal cells (e.g., Stro-1+; MSC); 2) osteoblasts (OB; optionally said osteoblasts provided by differentiating mesenchymal cells to differentiated osteoblasts); 3) arterial endothelium (e.g., CD146+NG2+; AEC); and 4) sinusoidal endothelium (CD146+NG2−; SEC), wherein each of said two or more populations of cells are provided in a separate chamber of the microfluidic device.

In some embodiments, the mesenchymal cells, osteoblasts, arterial endothelium, and/or sinusoidal endothelium cells are adult human bone marrow mononuclear cells.

In some embodiments, the populations of cells share a common media.

In some embodiments, the populations of cells are provided in a hydrogel carrier (e.g., a hyaluronic acid-based hydrogel), optionally wherein the hydrogel carrier is crosslinked (e.g., UV crosslinked).

In some embodiments, the populations are patterned to form a circular construct within the chambers of the microfluidic device. In some embodiments, the populations are patterned to form a channel that allows fluid flow around or through each of the populations of cells in the chambers.

In some embodiments, test cells may be infused into the construct and through each of the chambers. In some embodiments, the test cells may include malignant blood cells or circulating tumor cells from a patient.

In some embodiments, U937 cells infused into the construct show a preference for engrafting in the AEC population. In some embodiments, MOLM13 cells infused into the construct show a preference for engrafting in the OB and/or SEC populations. In some embodiments, CD34+ HSPC cells infused into the construct show a preference for engrafting in the OB and/or SEC populations.

In some embodiments, the microfluidic device comprises a common inlet in fluid communication with each of the chambers. In some embodiments, the common inlet is equidistant to each of the chambers.

In some embodiments, the chambers are connected by microchannels (e.g., endothelialized microchannels).

In some embodiments, the microfluidic device comprises an LED and/or CCD detector positioned to allow images of labeled cells in contact with the one or more chambers to be imaged and/or quantified in real time.

In some embodiments, the two or more populations of cells of the microfluidic device are from the same subject.

Also provided is a system comprising an in vitro construct as taught herein, a pump, a media reservoir, and associated tubing. In some embodiments, the system is a closed, recirculating system.

Also provided is a method of making an in vitro construct as taught herein, which may include: providing a microfluidic device as taught herein or a layer thereof having multiple chambers; and depositing into the chambers the two or more populations of cells (e.g., 3 or 4 populations of cells) (or "niches") selected from: 1) mesenchymal cells (e.g., Stro-1+; MSC); 2) osteoblasts (optionally said osteoblasts provided by differentiating mesenchymal cells to differentiated osteoblasts); 3) arterial endothelium (e.g., CD146+NG2+; AEC); and 4) sinusoidal endothelium (CD146+NG2−; SEC), wherein each of said two or more populations of cells are deposited into a separate chamber of the microfluidic device.

In some embodiments, the depositing is carried out by bioprinting a composition comprising one of the populations of cells into a chamber of the microfluidic device. In some embodiments, the composition comprises a hydrogel.

In some embodiments, the depositing is patterned depositing.

In some embodiments, the two or more populations of cells are provided in a hydrogel carrier, and the method further comprises patterned crosslinking of the hydrogel in the chambers.

In some embodiments, the depositing and/or crosslinking is patterned to form a channel that allows fluid flow around or through each of the populations of cells.

In some embodiments, the method further comprises endothelializing some or all of the channels.

Further provided is a method of detecting a cellular response to test cells and/or active agent(s) in a hematopoietic microenvironment, which may include: (a) providing a microfluidic device as taught herein; (b) optionally circulating a medium (e.g., a common medium) through the channels and chambers of the microfluidic device; (c) administering the test cells and/or active agent(s) to the niches in the device (e.g., by adding into medium through a common inlet in fluid communication with the niches), or irradiating one or more of the niches of the device with ionizing radiation (IR); and (d) detecting a cellular response to the test cells and/or active agent(s), or IR (e.g., determining a difference in interactions of infused cells with the respective niches).

In some embodiments, detecting the cellular response comprises comparing the response to the response (or lack of a response) observed when active agent(s) (e.g., chemotherapy drug(s)) are administered with the test cells (e.g., blood cells or circulating tumor cells, normal (non-cancerous) cells, etc.).

In some embodiments, the circulating is carried out in some or all of the channels at a physiological flow rate (e.g., from about 0.01 to about 10 mm/sec).

In some embodiments, the administering is carried out with cells that are labeled (e.g., fluorescently labeled) and the detecting is carried out by detecting the signal (e.g., fluorescence) thereof.

In some embodiments, the administering is carried out with normal (non-cancerous) HSPC. In some embodiments, the administering is carried out with malignant HSPC. In some embodiments, the malignant HSPC are from the same subject as the two or more populations of cells of the microfluidic device.

In some embodiments, the administering comprises administering cells and the cells are labeled with a detectable group and/or a genetic barcode.

BRIEF DESCRIPTION OF THE DRAWINGS

FIG. 1A: Microfluidic device fabrication is performed by layering of slides, adhesive films, and PMMA layers in which channels and chamber features are defined using a laser cutter. FIG. 1B: In situ 3D microconstruct formation workflow. Channels (i) are filled with a mixture of photocurable hydrogel precursor, cells, and additional components (ii). A photomask (shown as grey rectangle) is employed to define construct shape (ii). Following UV exposure, cross-linked hydrogels are formed in the chambers (iii), and the remaining solution is replaced with clean buffer/media (iv). FIG. 1C: Side and top view depictions of the patterned niche construct in a device chamber. FIG. 1D-FIG. 1E: Schematic and photograph of operational recirculating niche-on-a-chip system.

FIG. 3Ai-iii: The transmembrane receptor EPHB4 is exclusively present in the bone marrow sinusoidal tissue. FIG. 3Bi-iii: Endothelial cells in the bone marrow (arterial) characteristically express the ligand ephrin-B2. FIG. 3C-i: Alizarin red detects calcium deposition due to mineralization by the osteoblast. FIG. 3C-i is a staining on day three before infusion. FIG. 3Cii-iii: A brighter calcium deposition on day five after infusion of Qtrack labeled cells. FIG. 3Di-ii: CD44 is one of the principal cell membrane proteins in MSCs. FIG. 3D-i shows a green CD44 immunofluorescence label in the MSC construct after infusion of Qtrack labeled cells. Scale bar—100 µm.

FIG. 4A: Quantification of the red particles (size inclusion of 25-225 µm^2 and 1.0 circularity) inside the borders of the correspondent niche construct. FIG. 4B Experiments were terminated by day five. The final day quantification data demonstrates statistical difference between arterial and sinusoidal niche engraftment preference, also between arterial/MSC, osteoblast/sinusoidal and arterial/osteoblast (*P<0.05; **P<0.1, N=5).

DETAILED DESCRIPTION

Figure 1A:
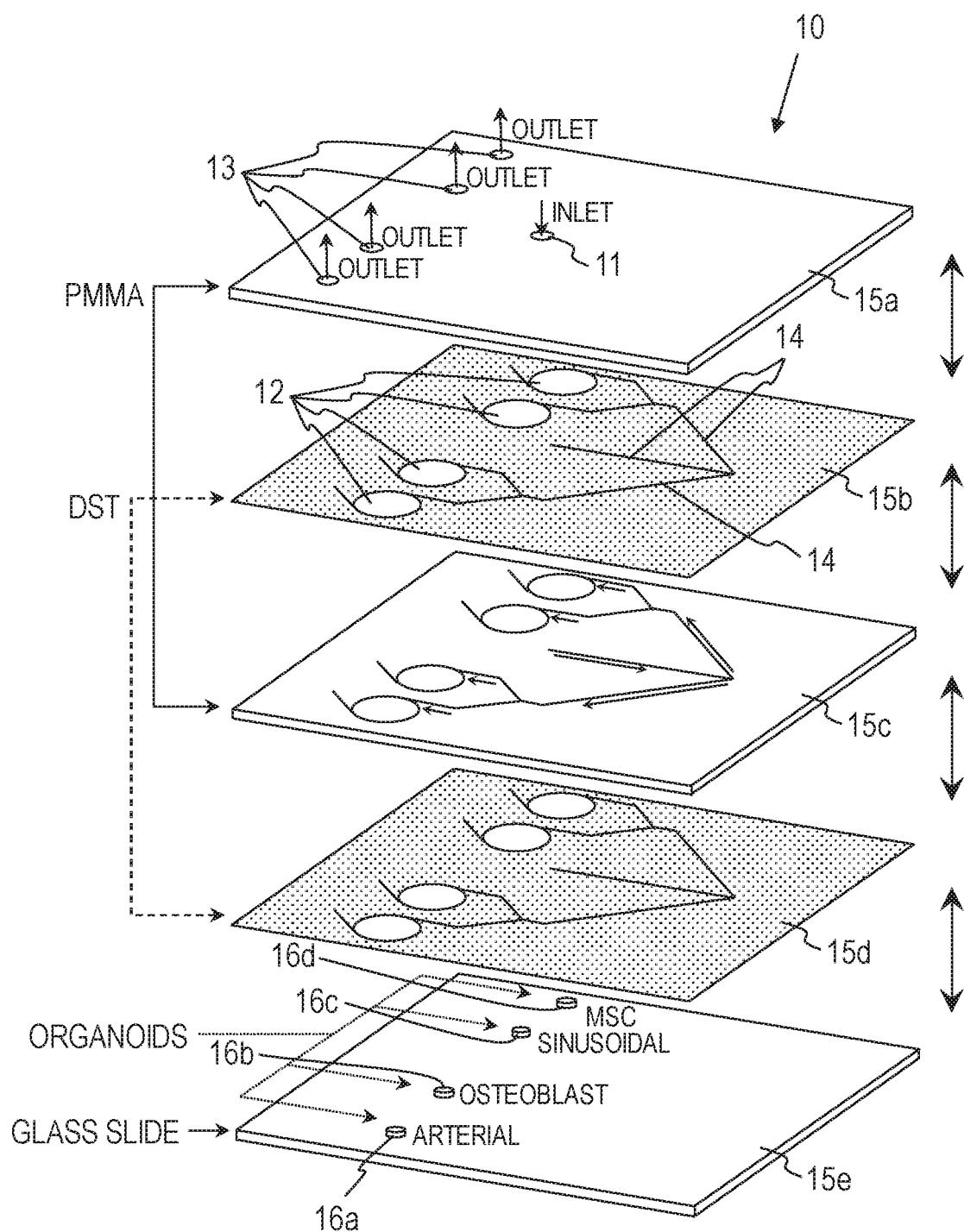
FIG. 1A-FIG. 1E. Microfluidic "chip" device fabrication and niche construct integration.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity. All publications, patent applications, patents and other references mentioned herein are incorporated by reference in their entirety. In case of a conflict in terminology, the present specification is controlling.

As used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations off 10%, ±5%, ±1%, ±0.5%, or even ±0.1% of X. A range provided herein for a measureable value may include any other range and/or individual value therein.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

"Three dimensional tissue construct" and "organoid" are used interchangeably herein and, as used herein, refer to a composition of live cells, typically in a carrier media, arranged in a three-dimensional or multi-layered configuration (as opposed to a monolayer). Suitable carrier media include compositions of the present invention (e.g., hydrogels, such as cross-linked hydrogels, of the present invention). In some embodiments, an organoid is about 100 μm or 200 μm to about 350 or 500 μm in diameter, such as, for example, about 100, 150, 200, 250, 300, 350, 400, 450, or 500 μm. The organoid may comprise about 1,500, 2,000, 5,000 to about 10,000, 25,000, or 50,000 cells in total or about 1,000, 5,000, 10,000, or 50,000 to about 75,000, 100,000, or 150,000 cells in total.

"Cells" used in the present invention are, in general, animal cells, particularly mammalian and primate cells, examples of which include but are not limited to human, dog, cat, rabbit, monkey, chimpanzee, cow, pig, or goat. The cells are preferably differentiated at least in part to a particular cell or tissue type, such as liver, intestine, pancreas, lymph node, smooth muscle, skeletal muscle, central nerve, peripheral nerve, skin, immune system, etc. Some cells may be cancer cells, as discussed further below, in which case they optionally but preferably express (naturally, or by recombinant techniques) a detectable compound, as also discussed further below.

Cells may be obtained from established cultures, donors, biopsy, or a combination thereof. In some embodiments, cells are stem cells or progenitor cells (e.g., HSPC or MSC). In some embodiments, cells are primary cells. In some embodiments, cells are passaged.

In some embodiments, cells are human cells. In some embodiments, cells are bone marrow cells, which may be obtained/collected from adult human bone marrow mononuclear cells.

"Subjects" as used herein are, in general, human subjects, although aspects of the invention may be implemented with other animal subjects, particularly mammalian subjects (e.g., dogs, cats, horses, goats, sheep) for veterinary purposes. Subjects may be male or female and of any age, including infant, juvenile, adolescent, adult, and geriatric.

"Media" as used herein may be any natural or artificial growth media (typically an aqueous liquid) that sustains the cells used in carrying out the present invention. Examples include, but are not limited to, an essential media or minimal essential media (MEM), or variations thereof such as Eagle's minimal essential medium (EMEM) and Dulbecco's modified Eagle medium (DMEM), as well as blood, blood serum, blood plasma, lymph fluid, etc., including synthetic mimics thereof. In some embodiments, the growth media includes a pH color indicator (e.g., phenol red).

The "hematopoietic microenvironment" refers to the interactions of hematopoietic stem/progenitor cells (HSPC) residing within specific bone marrow (BM) niches on a cellular level.

A "bone marrow niche" is a microenvironment comprising particular groups of bone marrow cells or cell types. See, e.g., US 2011/0207166 to Vaiselbuh.

"Mesenchymal cells" or "mesenchymal stem cells" ("MSC") are stem cells that can differentiate into a variety of cell types, such as osteoblasts, chondrocytes, myocytes, and adipocytes. In some embodiments, the MSC are from bone marrow. In some embodiments, MSC are sorted from bone marrow cells. In some embodiments, MSC are positive for Stro-1 (i.e., Stro-1+). In some embodiments, the MSC are positive for CXCL12 (i.e., CXCL12+). In some embodiments, the MSC are positive for nestin (i.e., nestin+). In some embodiments, the MSC are positive for stem cell factor (SCF) (i.e., SCF+). In some embodiments, the MSC are negative for CD34 (i.e., CD34−).

"Osteoblasts" are mononuclear cells that may produce bone. In some embodiments, osteoblasts used herein are provided by differentiating MSC. In some embodiments, osteoblasts are sorted from bone marrow cells (e.g., based on alkaline phosphatase expression). In some embodiments, osteoblasts are positive for calcium deposition. In some embodiments, osteoblasts are positive for osteocalcin. In some embodiments, osteoblasts are positive for osteonectin.

"Arterial endothelium" cells ("AEC") are endothelial cells that may form the inner lining of blood vessels. In some embodiments, the AEC are from bone marrow. In some embodiments, AEC are sorted from bone marrow cells. In some embodiments, AEC are positive for CD146 (i.e., CD146+). In some embodiments, the AEC are positive for NG2 (i.e., NG2+). In some embodiments, the AEC are positive for CXCL12 (i.e., CXCL12+). In some embodiments, AEC are CD146+ and NG2+. In some embodiments, AEC are CD146+, CXCL12+ and NG2+.

"Sinusoidal endothelium" cells ("SEC") are microvascular endothelial cells with specialized functions. In some embodiments, the SEC are from bone marrow. In some embodiments, SEC are sorted from bone marrow cells. In some embodiments, SEC are positive for CD146 (i.e., CD146+). In some embodiments, SEC are negative for NG2 (i.e., NG2−). In some embodiments, the SEC are positive for CXCL12 (i.e., CXCL12+). In some embodiments, SEC are CD146+ and NG2−. In some embodiments, SEC are CD146+, CXCL12+ and NG2−.

In some embodiments, cells may be provided and/or bioprinted in a carrier such as a hydrogel carrier. "Hydrogel," as used herein, may be any suitable hydrogel. In general, the hydrogel includes water and is further comprised of or derived from polyalkylene oxides, poloxamines, celluloses, hydroxyalkylated celluloses, polypeptides, polysaccharides, carbohydrates, proteins, copolymers thereof, or a combination of two or more thereof, and more particularly are comprised of or derived from poly(ethylene glycol), poly(ethylene oxide), poly(vinyl alcohol), poly(vinylpyrrolidone), poly(ethyloxazoline), poly(ethylene oxide)-co-polypropylene oxide) block copolymers, carboxymethyl cellulose, hydroxyethyl cellulose, methylhydroxypropyl cellulose, polysucrose, hyaluronic acid, dextran, heparan sulfate, chondroitin sulfate, heparin, alginate, gelatin, collagen, albumin, ovalbumin, copolymers thereof, or a combination of two or more thereof, all of which may be crosslinked to varying degrees in accordance with known techniques, or variations thereof that are apparent to those skilled in the art. See, e.g., U.S. Pat. Nos. 8,815,277; 8,808,730; 8,754,564; 8,691,279.

In some embodiments, the hydrogel comprises hyaluronic acid, collagen, fibronectin, laminin, alginate, and/or gelatin. In some embodiments, the hydrogel may be crosslinked. In some embodiments, the hydrogel may include a crosslinkable prepolymer and/or post-deposition crosslinking group, which groups may be crosslinked before and/or after deposition thereof. See, e.g., WO 2016/064648 to Skardal et al., which is incorporated by reference herein.

In some embodiments the carrier may include extracellular matrix (ECM) derived from bone marrow tissue. In some embodiments, the carrier may include human derived ECM (e.g., ECM derived from human bone marrow tissue.) In some embodiments, the carrier may include niche-specific ECM.

In some embodiments, the carrier is an extrudable or otherwise bioprintable composition ("bioink"). See WO 2016/064648 to Skardal et al., which is incorporated by reference herein. In some embodiments, bioink may be comprised of a cross-linkable polymer (e.g., thiol-acrylate polymer), a post-deposition crosslinking group or agent (e.g., UV-activated crosslinking groups such as alkynes); and other optional ingredients, including but not limited to growth factors, initiators (e.g., of cross-linking), water (to balance), etc. In some embodiments, the bioink compositions are in the form of a hydrogel.

Depositing or seeding of the cells to form the niches can be carried out by any suitable technique, including but not limited to, spreading/painting, coating, spraying, etc. In some embodiments, the depositing steps are carried out by printing (or "bioprinting") in accordance with any suitable technique, including both "ink jet" type printing and syringe injection type printing. Apparatus for carrying out such bioprinting is known and described in, for example, Boland et al., U.S. Pat. No. 7,051,654; Yoo et al., US Patent Application Pub. No. US 2009/0208466; and Kang et al., US Patent Application Publication No. US 2012/0089238. In some embodiments, the depositing is a patterned depositing; that is, deposition is carried out so that the deposited composition is deposited in the form of a regular or irregular pattern, such as a regular or irregular lattice, grid, spiral, etc. In some embodiments, deposited cell-containing compositions are crosslinked in a particular pattern or shape (e.g., oval or elliptical), which may be done, e.g., with the use of photomasks during UV crosslinking.

Various aspects and features of the inventions described herein can be implemented in accordance with known materials, methods and techniques, or variations thereof that will be apparent to those skilled in the arts to which the present inventions pertain. See, e.g., Skardal A, Devarasetty M, et al. A reductionist metastasis-on-a-chip platform for in vitro tumor progression modeling and drug screening. Biotechnology and Bioengineering 113(9), 2020-32 (2016); Skardal A, Devarasetty M, et al. A hydrogel bioink toolkit for mimicking native tissue biochemical and mechanical properties in bioprinted tissue constructs. Acta Biomaterialia 25, 24-34 (2015); Bhise N, Manoharan V, et al. A liver-on-a-chip platform with bioprinted hepatic spheroids. Biofabrication 8(1); 014010 (2016).

In some embodiments, and with reference to FIG. 1A, the microfluidic device (10) contains two or more separate chambers (12) (e.g., 2, 3, 4 or 5 chambers), which chambers (12) may comprise a particular niche or population of bone marrow cells ("organoid") (16) as taught herein. In some embodiments, the chambers (12) are in fluid communication with each other by way of channels (14) and share a common aqueous growth media. In some embodiments, the niches (16) are viable for at least 1, 2, 3, 4, or more weeks, such that they may comprise at least about 75% or more (e.g., about 80%, 85%, 90%, 95% or more) living cells based on the average number of cells present in the construct, at 1, 2, 3, 4, or more weeks.

Figure 1B:
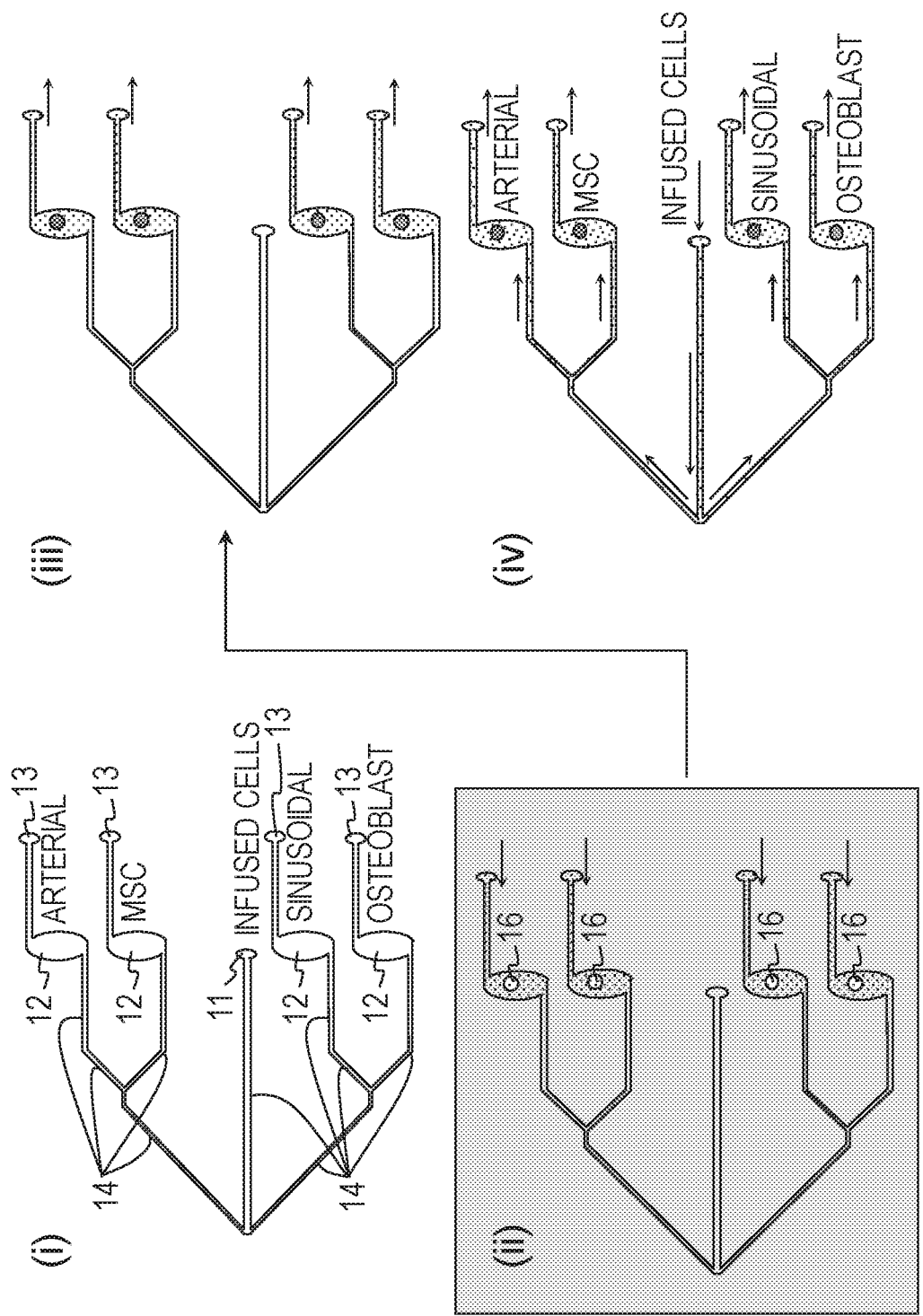
Figure 1C:
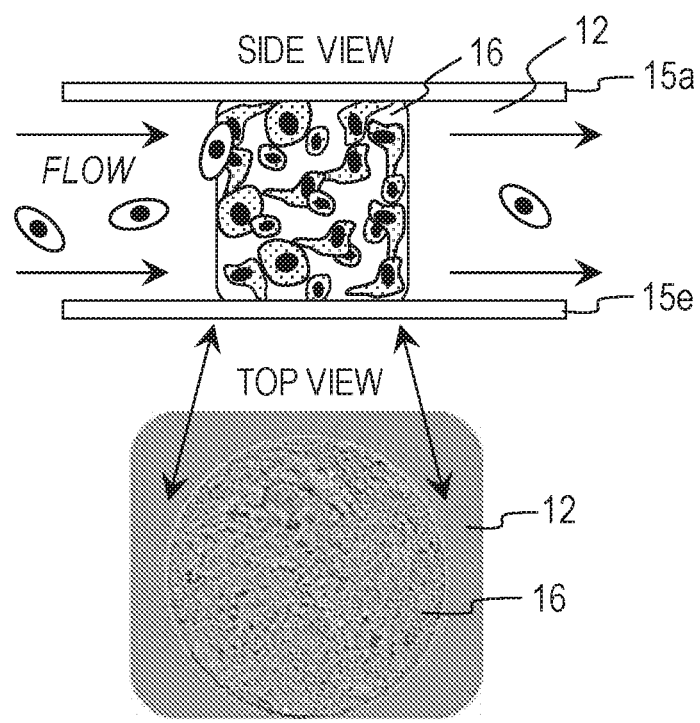
Figure 5A:
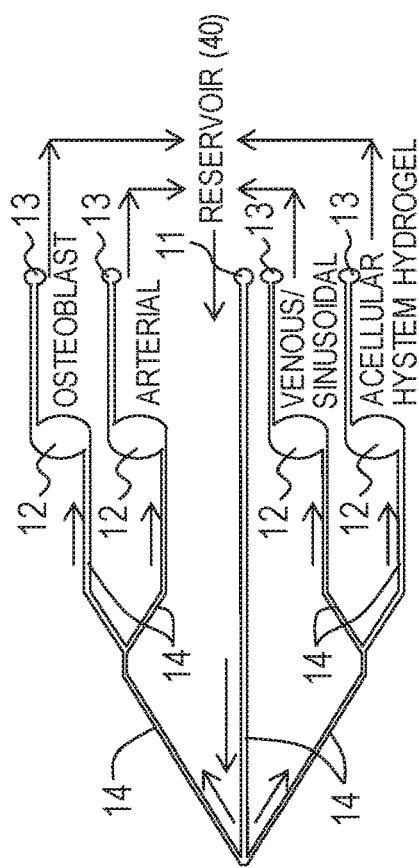
FIG. 5A-FIG. 5B present a schematic (FIG. 5A) and construction of "vascularized" BM niches (FIG. 5B).
Figure 5B:
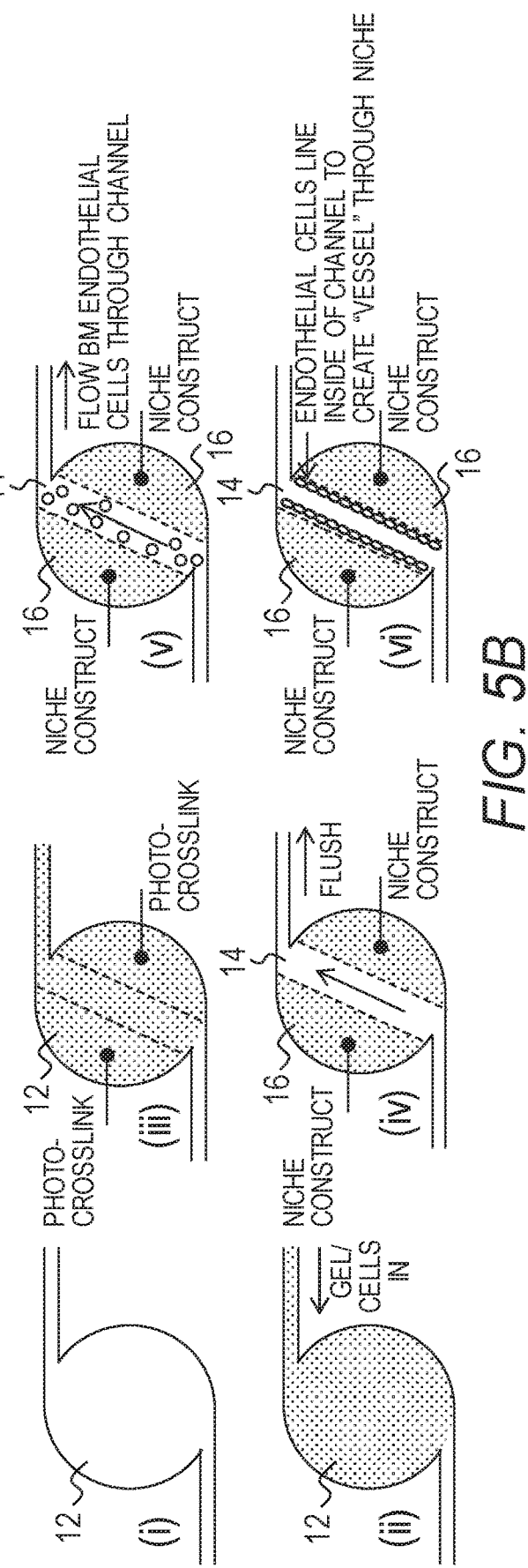

With reference to FIG. 1B, FIG. 1C and FIG. 5B, cells may be deposited in a chamber (12), followed by photopatterned crosslinking to form an organoid (16). As formed, in each chamber (12) there may be a channel (14) allowing fluid flow around the organoid (16).

The device body (15) of the microfluidic device may be formed of any suitable material or combination of materials and/or layers. Examples include, but are not limited to, polydimethylsiloxane (PDMS), polystyrene, polymethyl methacrylate (PMMA), polyacrylamide, polyethylene glycol (PEG) including functionalized PEG (e.g., PEG diacrylate, PEG diacrylamide, PEG dimethacrylate, etc., or any of the foregoing PEGs in multi-arm forms, etc.), natural polymers or proteins that can be cross-linked or cured (e.g., hyaluronic acid, gelatin, chondroitin sulfate, alginate, etc.). The device body may be formed by any suitable process, including molding, casting, additive manufacturing (3d printing), lithography, etc., including combinations thereof. In some embodiments, tape (15b, 15d) (e.g., silicone tape or adhesive films) can be used as layers to form chambers (12) and/or channels (14) in the device body (15). The tape may be self-aligned through folding and layered to form microfluidic structures. See FIG. 1A. See also, e.g., Temiz et al., Lab-on-a-chip devices: How to close and plug the lab? Microelectronic Engineering, 2015. 132: p. 156-175; Cosson et al., Ultra-rapid prototyping of flexible, multi-layered microfluidic devices via razor writing. Lab Chip, 2015. 15(1): p. 72-6.

Figure 1D:
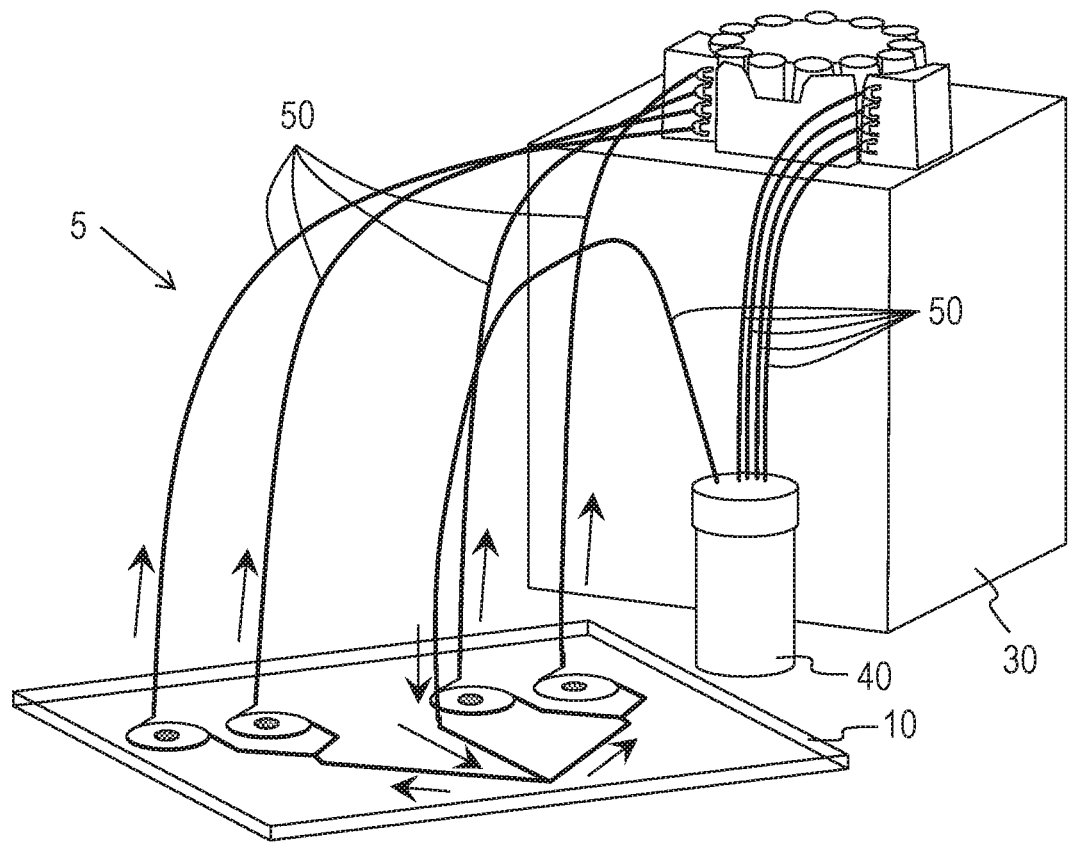
Figure 1E:
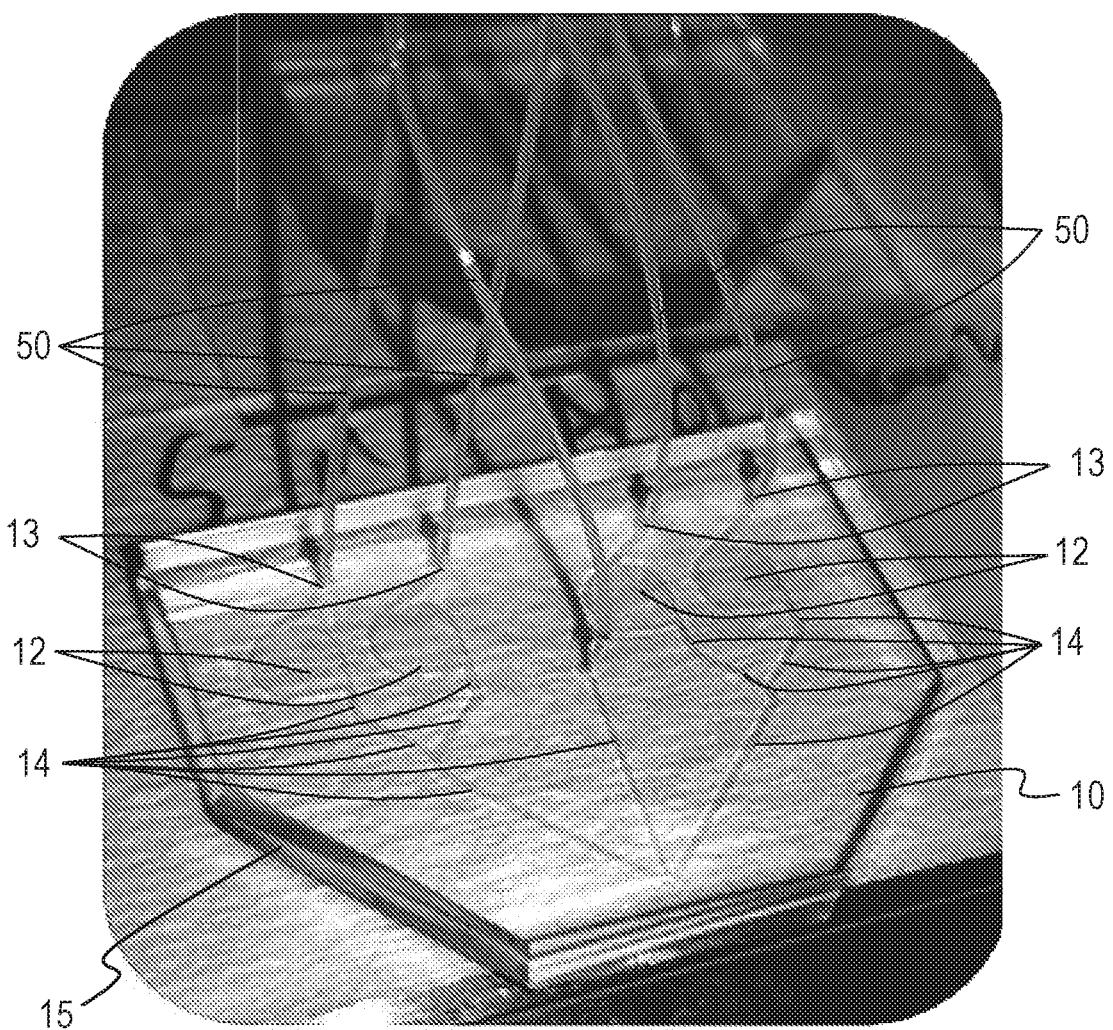

As may be seen in FIG. 1D, the microfluidic device (10) carrying the chambers (12), associated niches (16), inlets (11), outlets (13), and channels (14), may be provided in the form of an independent "cartridge" or subcombination that may be installed within a larger apparatus or "system" (5) in combination with additional components for use. Thus, in some such larger system (5) embodiments, the system (5) further includes a pump (30) operatively associated with the device (10) for circulating media through the channels (14) and chambers (12), and may also include a media reservoir (40), and associated tubing (50), also in operative association with the device (10) and pump (30). In some embodiments, the system is a closed, recirculating system.

In some embodiments, the microfluidic device (10) includes a common inlet (11) in fluid communication with each of the chambers (12). In some embodiments, the common inlet (12) has a fluid path (shown by arrows) through the microfluidic device, e.g., by microchannels (14) in the device, which path may be equidistant to each of the chambers. See FIG. 1A, FIG. 1B, and FIG. 5A. In some embodiments, media and/or cells may be infused into the common inlet (11) for fluid communication with each of the chambers (12).

In some embodiments, the chambers (12) are in fluid communication by way of channels (14) that are endothelialized (i.e., contain a layer of endothelial cells). In other embodiments, the channels (14) are not endothelialized. By way of example, to endothelialize microchannels, the luminal side of the channel may be seeded with endothelial cells, such as primary human BM-derived endothelial cells (BMEC; which may be flow-sorted from BMNC based on the phenotype CD31+CD144+TIE2+), through which fluid and cells can flow. For example, after the system is constructed, endothelial cells can be perfused through the system, then flow can be slowed/halted to allow endothelial cells to adhere to surfaces of the channels and/or niches. Flipping the device and repeating may occasionally be necessary to enhance coverage. The microfluidics of each chip may then be attached to a micro-peristaltic pump and media reservoir for driving flow through the circuit, thereby acting as a simplified circulatory system.

As noted above, the device may be provided as a cartridge, or as a subcombination unit or "building block" configured in a manner suitable for "snap in" installation in a larger apparatus including pumps, detectors, or the like. Once produced, such subcombination or "cartridge" devices may be used immediately, or prepared for storage and/or transport.

To store and transport the device, a transient protective support media that is a flowable liquid at room temperature (e.g., 25° C.), but gels or solidifies at refrigerated temperatures (e.g., 4° C.), such as a gelatin mixed with water, may be added into the device to substantially or completely fill the chamber(s), and preferably also any associated conduits. Inlet and outlet ports may be capped with a suitable capping element (e.g., a plug) or capping material (e.g., wax). The device may then be packaged together with a cooling element (e.g., ice, dry ice, a thermoelectric chiller, etc.) and all placed in a (preferably insulated) package.

Alternatively, to store and transport the device, a transient protective support media may be used that is a flowable liquid at cooled temperature (e.g., 4° C.), but gels or solidifies at warmed temperatures such as room temperature (e.g., 20° C.) or body temperature (e.g., 37° C.), such as poly(N-isopropylacrylamide) and poly(ethylene glycol) block co-polymers.

Upon receipt, the end user may remove the device from the associated package, allow the temperature to rise or fall (depending on the choice of transient protective support media), uncap ports, and remove the transient protective support media with a syringe (e.g., by flushing with growth media).

Figure 6:
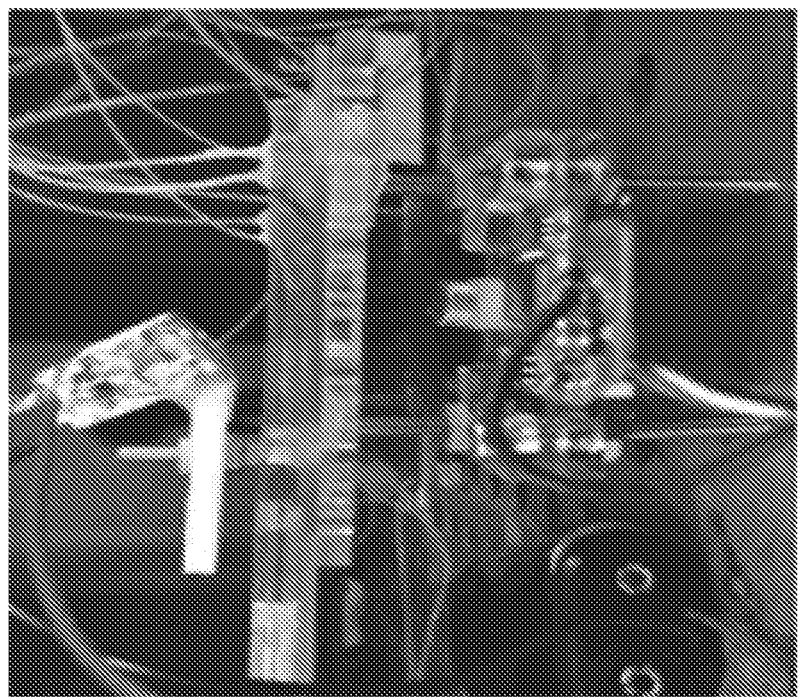
FIG. 6. Schematic and photograph of onboard LED/CCD-based detector of fluorescence imaging in real time.
Figure 6:
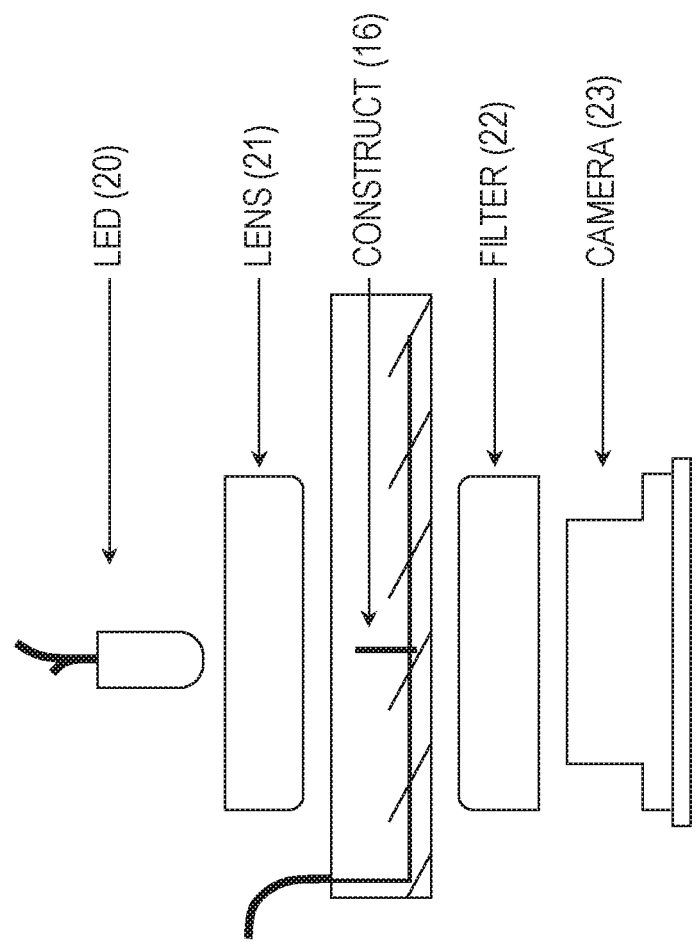

In some embodiments, and with reference to FIG. 6, at least a portion of the microfluidic device body (15), particularly including the portion containing an organoid (16), is transparent, and the device may further comprise a detector (23) (e.g., a camera, LED/CCD detector) operatively associated with one or more of the chambers (12) and configured for detecting (e.g., imaging) cells therein. In some embodiments, the detector (23) may be positioned to allow images of labeled cells in contact with the one or more chambers to be imaged and/or quantified in real time. An illuminating device (20) (e.g., an LED) may be provided on the side opposite of the detector (23). In some embodiments, a filter (22) may be provided, e.g., to focus the detection only on the organoid and/or block out signal from transient cells flowing through the channels (14) of the chamber (12). In some embodiments, the detector (23) may capture images (e.g., fluorescent images) at predetermined intervals, capturing incidences of colonization and growth of fluorescently labeled or luminescent cells from circulation in each niche, enabling real-time observation and/or quantitation of circulating cells and their preferential colonization of specific niches.

A microfluidic device of the present invention may be used in a method of in vitro testing of bone marrow niche interactions, interactions of infused cells with the niches (e.g., normal or malignant HSPC), drug screening, toxicology screening, and/or disease modeling. The method may comprise providing a microfluidic device of the present invention, and detecting cellular response and/or interaction in the chambers. In some embodiments, the method may comprise:

(a) providing a microfluidic device of the present invention;

(b) optionally circulating a medium (e.g., a common medium) through the chambers of the microfluidic device;

(c) administering test cells and/or active agent(s) to the niches in the device (e.g., by adding into medium through a common inlet in fluid communication with the niches), or irradiating the niches of the device with ionizing radiation (IR); and (d) detecting a cellular response to the test cells and/or active agent(s), or IR (e.g., determining a difference in interactions of infused cells with the respective niches). In some embodiments, detecting the cellular response may include comparing the response to the response (or lack of a response) observed when active agent(s) (e.g., chemotherapy drug(s)) are administered with cells (e.g., malignant cells).

In some embodiments, the circulating is carried out at a physiological flow rate in at least a portion of the device (e.g., "arterial" or side incoming to the niches; "venous" or outgoing side of the niches). In some embodiments, the physiological flow rate may be, for example, from about 0.01 to about 10 mm/sec, or from about 0.1 mm/sec to about 5 mm/sec. In some embodiments, the physiological flow rate may be from about 1 to about 3 mm/sec. In some embodiments, the physiological flow rate may be from about 0.1 to about 1 mm/sec.

In some embodiments, the administering is carried out with cells that are fluorescently labeled and wherein the detecting is carried out by detecting the fluorescence thereof.

In some embodiments, the administering is carried out with test cells comprising malignant blood cells or circulating tumor cells from a patient. In some embodiments, the administering is carried out with malignant HSPC test cells. In some embodiments, the administering is carried out with normal (non-cancerous) test cells (e.g., normal HSPC). In some embodiments, the test cells are from the same subject as the two or more populations of cells of the microfluidic device.

In some embodiments, cells are labeled and/or otherwise identifiable on a single cell basis, which may aid in understanding how individual hematopoietic stem cells contribute to blood formation. In some embodiments, HSC are "barcoded" in that each cell receives a specific tag ("bar code"), such as a genetic tag that is incorporated in their genome and is heritable to progeny. This may be done, for example, with a product such as the CellTracker™ Lentiviral Barcode Library (Cellecta, Mountain View, California). In so doing, each HSC and its progeny can be traced to the specific niches and allow evaluation of clonal heterogeneity of normal and leukemic hematopoiesis to respective niches.

The present invention is explained in greater detail in the following non-limiting Examples.

EXAMPLES

Example 1

We have shown that "on-a-chip" technologies using 3D human tissue constructs, in the presence of physiological flow conditions, can model normal physiology and disease processes and, more importantly, allow for drug screening. See Skardal, A., et al. (2016). "Organoid-on-a-chip and body-on-a-chip systems for drug screening and disease modeling." Drug Discov Today 21(9): 1399-1411; Skardal, A., et al. (2016). "A reductionist metastasis-on-a-chip platform for in vitro tumor progression modeling and drug screening." Biotechnol Bioeng 113(9): 2020-2032; Skardal, A., et al. (2017). "Multi-tissue interactions in an integrated three-tissue organ-on-a-chip platform." Scientific Reports 7: 8837.

In the present study, we sought to exploit the high physiological relevance and single cell resolution offered by "on-a-chip" technology to recreate the BM microenvironment in vitro and study, in real-time, the interactions of normal and malignant HSC with each specific niche cell type. To accomplish this objective, we constructed a microfluidic platform using polydimethylsiloxane (PDMS) and photolithography, in which microchannels allow continuous flow of media and HSPC through each of the specific niches, reproducing, in effect, a primitive circulatory system. To recreate the various BM niches, mesenchymal cells (Stro-1+; MSC), arterial endothelium (CD146+NG2+; AEC), and sinusoidal endothelium (CD146+NG2−; SEC) were magnetically-sorted from adult human BM mononuclear cells. Once established, an aliquot of Stro-1+ cells were induced to undergo osteogenic differentiation, to generate differentiated osteoblasts (OB).

To create the in situ patterned 3D niche-on-a-chip (NOC), the chambers of the microfluidic device were filled with AEC, SEC, MSC, or OB embedded in a hyaluronic acid (HA)-based hydrogel, a photomask aligned in the center of the chambers, and UV-crosslinked. Once fabricated, the niche constructs were allowed to equilibrate for 3 days, under constant media flow using a four-channel precision microperistaltic pump. U937, MOLM13, and normal CD34$^+$ cells were each labeled with Qtracker 605, and independently perfused into the main channel of a separate NOC, from which they enter and evenly disperse into four equidistant chambers, each of which housed a distinct BM niche (AEC, SEC, MSC, or OB). Live/dead staining confirmed viability of the HSPC and niche cells for least 5 days following HSPC infusion, and immunocytochemistry demonstrated the continued expression of appropriate phenotypic markers by each respective niche cell. At 24 h post-infusion, U937 cells already exhibited a marked predilection for AEC, and this persisted throughout the 5-day observation period, with roughly 4.5-times more U937 cells engrafting within the AEC niche than the SEC or MSC niches, and 3-times more U937 cells engrafting within the AEC niche than the OB niche. In contrast, MOLM13 cells exhibited a marked preference for the MSC and SEC niches, a moderate affinity for the OB niche, and engrafted only minimally within the AEC niche. In contrast to malignant cells, normal CD34+ HSPC engrafted preferentially within the SEC and OB niches, exhibited moderate engraftment within the MSC niche, and did not engraft the AEC niche.

In conclusion, our studies establish the feasibility of using microfluidic "on-a-chip" technology to recreate the various niches within the BM microenvironment, and provide proof that this novel system can be used to study the interactions of normal and malignant HSPC with distinct cells of the niche. This system is used to delineate the signaling pathways responsible for the observed preferential HSPC/niche cell interactions, with the ultimate goal of using this knowledge to develop more effective treatments for hematological malignancies and to enhance engraftment following HSC transplant.

Example 2

Materials and Methods
Microfluidic Platform Fabrication

The microfluidic platform was built using PDMS (10:1 Sylgard 184 silicone elastomer and curing agent respectably, Dow Corning) and a glass slide (VWR, Radnor, PA); both treated and irreversibly bounded with $N_2$ plasma. A convex hemicylindrical microfluidic channel (120 μm height) was fabricated using a modified previously-reported standard photolithography technique. Briefly, a primary SU-8 2050 (MicroChem, Westborough, MA) wafer was generated by standard lithography. A primary PDMS device was generated by molding the square channel then the channels were sealed with a 40-μm PDMS membrane. The membrane in the channels was deformed into the channels by a vacuum negative pressure system, SU-8 was placed into them and also spin-coated evenly on a glass slide. Both SU-8 covered surfaces were bind and UV-cured from the top. A final PDMS channel mold was generated for the microfluidic layer.

Cells Sorting and Differentiation

Frozen Human Bone Marrow mononuclear stem cells were obtained from Stem Cell Technology (Lot #1507160920 Age 28/M Caucasian 77 kg 170 cm No smoker). Thawed cells were divided into two vials for Stro-1 and CD146$^+$ isolation by MiniMACS Separator kit (Miltenyi Biotec, Auburn, CA) according to manufacturer instructions. Briefly, Stro-1 cells were labeled with IgM anti human Stro-1 and incubated with anti-rat IgM micro beads. CD146$^+$ were isolated by anti-PE multisort micro beads labeling. Sorting was carried with MS magnetic Column, the positively obtained Stro-1 (Mesenchymal Stem cells, MSCs) cells were culture in MSCGM (Lonza) in fibronectin coated flasks. CD146$^+$ were further sorted into NG2 positive (Arterial) or negative cells (Sinusoidal). Cells were incubated with NG2-APC and APC micro beads, followed by MS magnetic Column sorting. Positively selected cells (NG2$^+$) and negatively selected cells (NG2$^-$) were individually culture in MSCGM in fibronectin coated flasks. Passage one of the Stro-1 cells was prepared to go under osteogenic differentiation (Osteoblast) with the StemPro Osteogenesis Differentiation Kit (Life Technologies). Shortly, at 50% confluency MSCGM media was exchanged for freshly prepared Osteocyte/chondrocyte differentiation basal media with supplements, osteoblasts were harvested at day for chip integration.

Individual Niches Construct Biofabrication

The in situ patterned stromal niches construct were based on a modified reported technique (Skardal, A., et al. (2015). "In situ patterned micro 3D liver constructs for parallel toxicology testing in a fluidic device." Biofabrication 7(3): 031001). Chambers were filled with Arterial, Sinusoidal, Osteoblast or MSCs cells encapsulated in thiol-modified hyaluronic acid (HA) based hydrogel (ESI-BIO, Alameda, USA), in their respective chamber. A photomask with four equidistant 500 micrometers diameter circles was aligned in the center of the chambers and UV light exposed for crosslinking, followed by PBS and serum free QBSF-60 Stem Cell Medium (Quality Biological, Gaithersburg, MD) washes to remove un-crosslink solution (FIG. 1B, FIG. 5B).

Fluidic Dynamics and Cellular Infusion

Upon fabrication, for three days, an open loop system was set up in a four-channel precision micro peristaltic pump (Elemental Scientific, Omaha, NE). Previous to infusion, U937, MOM13 and CD34$^+$ cells (ATCC, Manssas, VA) were independently labeled with the Qtracker 605 Cell Labeling Kit (Life Technologies, Carlsbad, CA) following manufacturer instructions. Shortly, a 10 nM labeling solution was prepared from component A and B. The solution was diluted in 0.2 mL of fresh complete growth medium. The cells were incubated in the solution for 45 minutes and washed twice with full media; 1×10$^{\char`\^}$6 cells mL$^{-1}$ in QBSF-60 were put into a fresh reservoir and bundle into the system. On the day of infusion, a close loop system was set up and labeled U937, MOM13 and CD34$^+$ cells were independently perfused to a BM chip at a flow rate of 570 µL hr$^{-1}$. Cells enter a main channel and evenly disperse into the four equidistant chambers with their respectively stromal niche.

Assessment of Cell Viability and Characterization

Cell viability was assessed with a LIVE/DEAD (L/D) viability/cytotoxicity kit (Life Technologies, Grand Island, NY) following modify manufacturer instructions. Briefly, in a 1:1 mixture of PBS and QBSF-60 media a concentration of 2 µM and 4 µM calcein-AM and ethidium homodimer-1 respectively was prepared. The solution was placed into a fresh reservoir and perfused into the system for thirty minutes Immunofluorescence staining for EPHB4, ephrin-B2 and CD44 were carried out inside the chip chambers using a standard protocol (Primary antibodies: Invitrogen 37-1800, Novus Biologicals NBP1-84830 and Abeam Anti-CD44(FITC) ab23557, respectively. Secondary antibodies: Invitrogen Alexa Flour 488 goat anti-mouse, Alexa Flour 594 goat anti-rabbit, for B4 and B2 respectably). All images were carried out using a fluorescence microscope (Leica DM4000B).

Molecule Quantification

Bright-field (BF)/Qtrack stacked images in TIFF format were captured and processed in ImageJ in the following manner: (1) Using oval or elliptical tools, the stromal construct area was selected. (2) Using Image|Duplicate, a new image was generated and the surrounding area of the construct was cleared (Clear outside). This generated "mask" was utilized on each remaining correspondent stromal construct. (3) Using Image|Color|Split Channels, a new image with the red labeled signals were separated from the composed BF/Qtrack image. (4) Using Image|Adjust|Threshold, the red signals borders were defined and colored black with a white background. (5) Using Analyze|Analyze Particles a constant size inclusion filter (25-225 µm$^{\char`\^}$2) with a circularity of 0.0-1.0 was applied to ensure that debris, noise signal and bright stromal cells were excluded.

Statistical Analysis

Statistical analysis was determined using unpaired heteroscedastic Students's t-test (2-tailed), and P<0.1 or less was considered statistically significant. Data are presented as means and standard deviation of at least n=4 or higher.

Results

Figure 2:
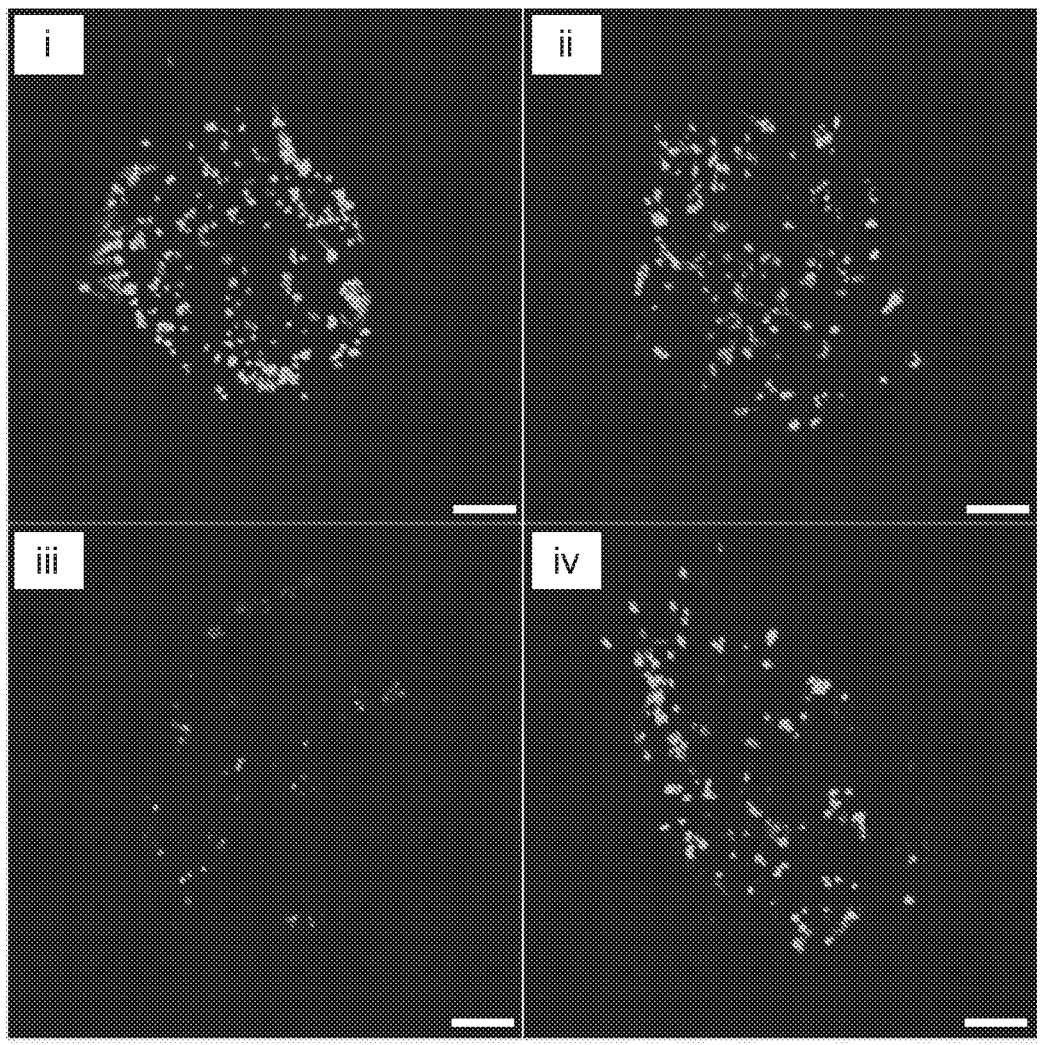
FIG. 2. Live/dead assay confocal imaging showing the viability of the photo-patterned constructs at day 3 before infusion. Calcein AM stains live cells with green fluorescence and dead cells are stained red with ethidium homodimer-1. (i) MSC construct. (ii) Arterial construct. (iii) Osteoblast construct. (iv) Sinusoidal construct; Scale bar—200 µm.

Bone marrow were partitioned into four central primary cell types. The cells were deposited with UV photo-patterning of the individual stromal tissues inside a 3D hydrogel environment, inside a microfluidics device. Due to the vigorous procedure, L/D assays (FIG. 2) were carried out in the different stromal constructs inside our microfluidic system to assess viability for 10 days. We observed a noticeable reduction in stromal tissue viability by day 8, defining the optimal length of our cell infusion experiments.

Figure 3A:
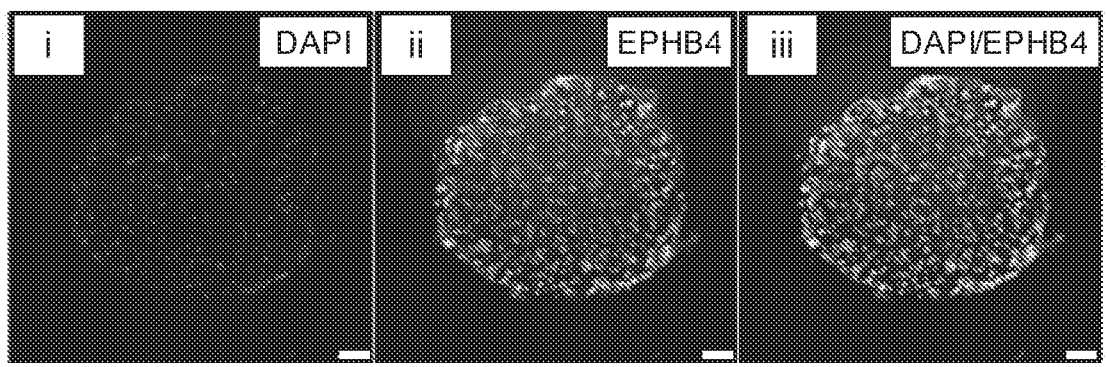
FIG. 3A-FIG. 3D. Niche constructs characterization inside their microfluidics chambers.
Figure 3B:
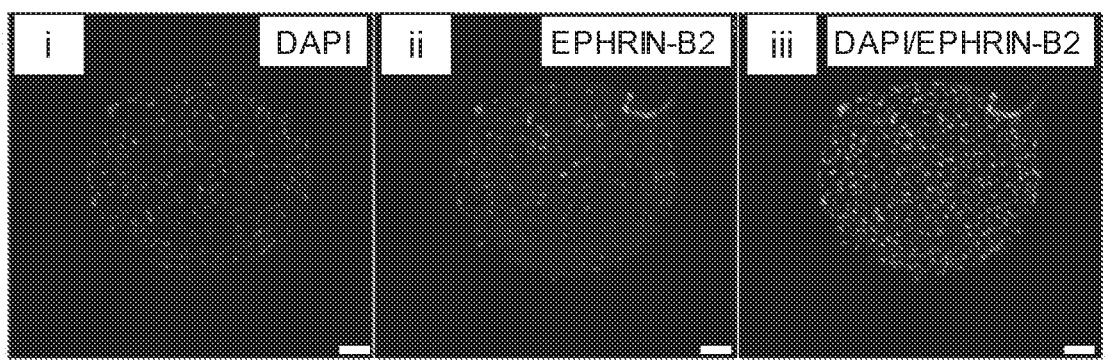
Figure 3C:
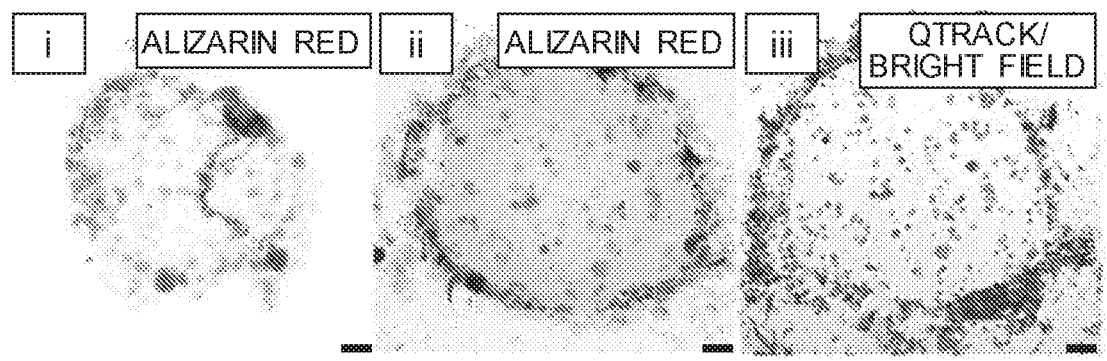
Figure 3D:
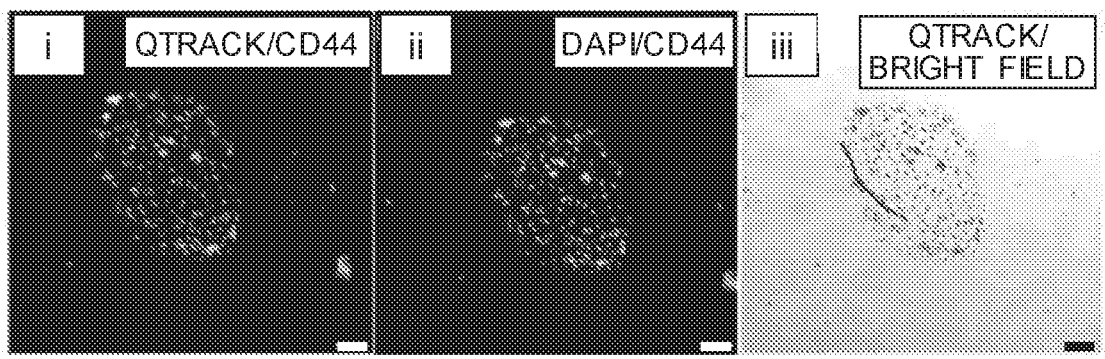

To assess maintenance of phenotype throughout the length of the experiment, each stromal tissue was stained for the transmembrane receptor EPHB4, ligand ephrin-B2, CD44 and Alizarin red histochemistry. Sinusoidal segregation from other hematopoietic cells in the bone marrow has been demonstrated by EPHB4 staining in both mice sinusoidal vessels and bone marrow cell extraction. Surrounding cells in the sinusoidal endothelium express ephrin-B2 and are positive for arterial markers without the receptor EPHB4. Surrounding ephrin-B2$^+$ endothelial cells play a role in angiogenesis, cell migration and adhesion, with a cell to cell interaction that helps hematopoietic cells mobilization inside the bone marrow. In our system previously sorted arterial and sinusoidal cells maintained their phenotype, shown by positive staining of EPHB4 and ephrin-B2 in their respective niche constructs (FIG. 3A and FIG. 3B). Stro-1 sorting is highly positive for MSCs but fine tuning between the endothelial counterpart inside the bone marrow is needed to assure multipotent lineage. CD44 is a membrane marker that is consistently positive in MSCs and negative on endothelial cells and hematopoietic stem cells. This staining persisted positive in our MSC niche regardless of lymphoma cell infusion (FIG. 3D). The same MSCs were differentiated into osteoblast, after 3 days in differentiation media the cells were harvested and built into a niche construct in the BM chip. Inside their niches healthy osteoblasts perform calcium deposition. A bright orange-red staining from Alizarin red treatment is an indicator of this deposition in the matrix. FIG. 3Ci-ii demonstrate an increase in this deposition over time from the osteoblast niche, regardless of the absence of osteoblast differentiation media.

Figure 4A:
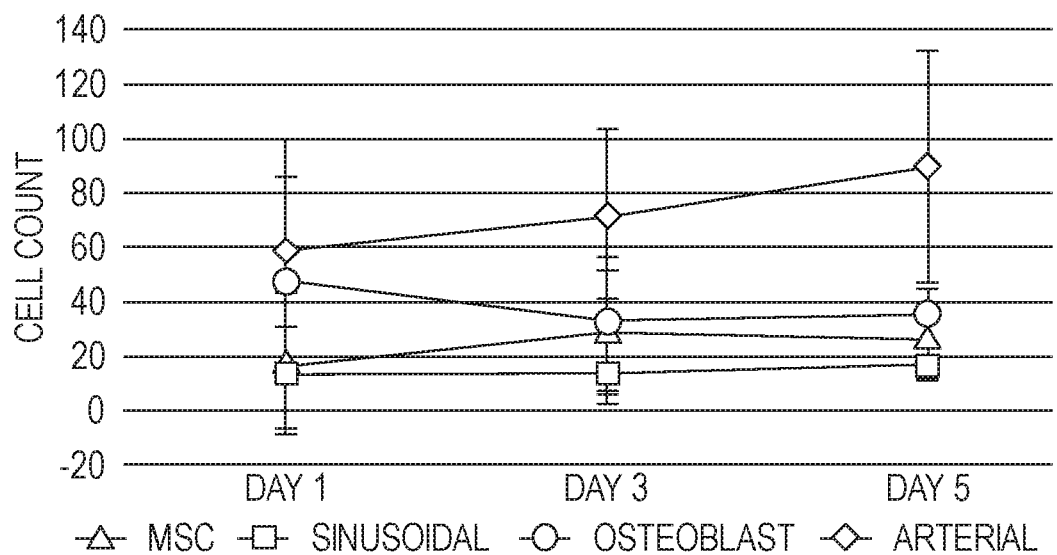
FIG. 4A-FIG. 4B. Characterization of specific niche engraftment by infusion of Qtrack labeled lymphoma cells U937.
Figure 4B:
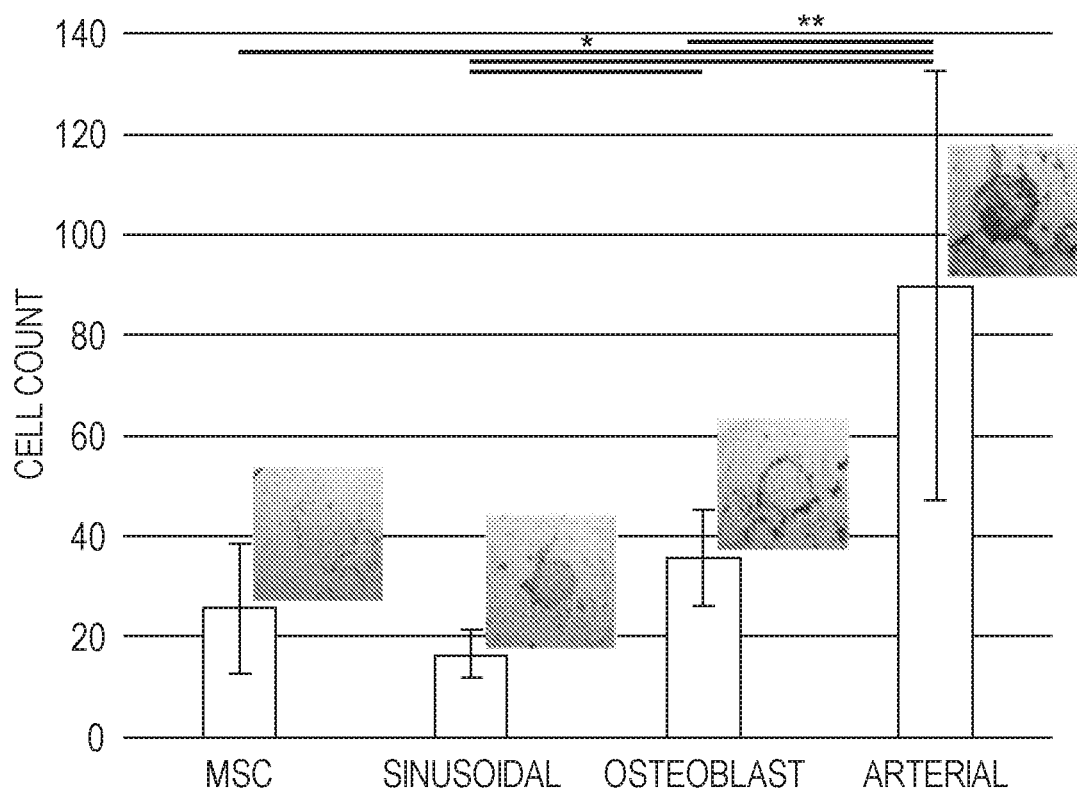

One of the most common cell lines to study monocytes differentiation are the U937, a human cell line derived from a patient with histiocytic lymphoma. As a cell with hematopoietic characteristics we selected them as a candidate to study niche engraftment preference. From day one of cell infusion into the BM chip we could notice an inclination toward the arterial niche (FIG. 4A), but no statistical significance was noticeable. By day five there is a significant engraftment and preference of the U937 cells toward the arterial niche (FIG. 4B), specially over the closest phenotypical niches, MSCs and sinusoidal. The lone selected Stro-1$^+$ cell derived constructs, osteoblast and MSCs, had no significant difference in niche engraftment preference by the hematopoietic cells.

REFERENCES

Kang E, Shin S J, Lee K H, Lee S H. Novel PDMS cylindrical channels that generate coaxial flow, and application to fabrication of microfibers and particles. Lab Chip. 2010 Jul. 21; 10(14):1856-61. doi: 10.1039/c002695f.

Skardal A, Devarasetty M, Soker S, Hall A R. In situ patterned micro 3D liver constructs for parallel toxicology testing in a fluidic device. Biofabrication. 2015 Sep. 10; 7(3):031001. doi: 10.1088/1758-5090/7/3/031001.

Zhang Y S, Aleman J, Shin S R, Kilic T, et al. Multisensor-integrated organs-on-chips platform for automated and continual in situ monitoring of organoid behaviors. Proc Natl Acad Sci USA. 2017 Mar. 21; 114(12):E2293-E2302. doi: 10.1073/pnas.1612906114. Epub 2017 Mar. 6.

Kwak H, Salvucci O, Weigert R, et al. Sinusoidal ephrin receptor EPHB4 controls hematopoietic progenitor cell mobilization from bone marrow. The Journal of Clinical Investigation. 2016; 126(12):4554-4568. doi:10.1172/JC187848.

Feda Azab, Abdel Kareem Azab, Patricia Maiso, Teresa Calimeri, et al. Eph-B2/Ephrin-B2 Interaction Plays a Major Role in the Adhesion and Proliferation of Waldenstrom's Macroglobulinemia. Clin Cancer Res Jan. 1 2012 (18) (1) 91-104; DOI: 10.1158/1078-0432.CCR-11-0111

Sawamiphak S, Seidel S, Essmann C L, Wilkinson G A, Pitulescu M E, Acker T, Acker-Palmer A. Ephrin-B2 regulates VEGFR2 function in developmental and tumour angiogenesis. Nature. 2010 May 27; 465(7297):487-91. doi: 10.1038/nature08995. Epub 2010 May 5.

L. Ramos T, Sanchez-Abarca L I, Muntion S, et al. MSC surface markers (CD44, CD73, and CD90) can identify human MSC-derived extracellular vesicles by conventional flow cytometry. Cell Communication and Signaling: CCS. 2016; 14:2. doi:10.1186/s12964-015-0124-8.

Lin G, Liu G, Banie L, et al. Tissue Distribution of Mesenchymal Stem Cell Marker Stro-1. Stem Cells and Development. 2011; 20(10):1747-1752. doi:10.1089/scd.2010.0564.

Sundström, C. and Nilsson, K. (1976), Establishment and characterization of a human histiocytic lymphoma cell line (U-937). Int. J. Cancer, 17: 565-577. doi:10.1002/ijc.2910170504

Example 3

FIG. 5A-FIG. 5B show particular patterning strategies for fabricating "vascularized" BM niche constructs within the device, providing a channel through the middle of the niche constructs themselves, the luminal side of which can then be seeded with primary human BM-derived endothelial cells, to create a vascular structure through which fluid and cells can flow. When expressing the appropriate adhesion molecules, cells migrating through this simple circulatory system may bind to the endothelium, extravasate, and colonize the niche construct.

FIG. 6 shows an integrated camera apparatus that may be used to detect BM niche/cell activity in the microfluidic device.

To produce the NoC, thin silicone tapes will be self-aligned through folding and layered to form microfluidic structures. To generate niche-specific ECMs, normal/healthy human BM mononuclear cells (BMNC; AllCells, LLC) will be FACS-sorted (Aria II, BD Biosciences) to obtain the following 3 populations: 1) "arterial" MSC (CD146+CXCL12+NG2+); 2) "venous/sinusoidal" MSC (CD146+CXCL12+NG2-); and 3) osteoblast progenitors (sort for Stro-1+ MSC and induce osteogenic differentiation). Alternatively, we will sort osteoblasts directly, based on alkaline phosphatase expression. Cells will then be culture expanded until sufficient numbers are obtained for the proposed experiments.

To produce the ECM, another aliquot of each cell type will be cultured in the presence of a macromolecular crowding (MMC) "cocktail" to stimulate robust synthesis of ECM. Each niche-specific ECM will be collected and then mixed with HyStem and the respective niche cell type, and the mixture introduced to its allotted microfluidic chamber. Patterning will then be accomplished using a positive-tone photomask to define the shape and location of each polymerized construct, and the constructs washed/flushed to create a channel through each niche. The luminal side of this channel will be seeded with primary human BM-derived endothelial cells (BMEC; flow-sorted from BMNC based on the phenotype CD31+CD144+TIE2+), to create a vascular structure through which fluid and cells can flow.

The microfluidics of each chip will then be attached to a micro-peristaltic pump and media reservoir for driving flow through the circuit, thereby acting as a simplified circulatory system. Serum-free media will then be flowed through the chips at a rate of 5-30 µl/min. Niches will be left to equilibrate for 1 wk before adding HSPC.

Hematopoietic repopulation of niches: Three distinct populations of hematopoietic stem and progenitor cells will be isolated by combining magnetic bead depletion/selection (Miltenyi) and multicolor flow cytometric sorting: 1) HSC (Lin-CD34+CD38-CD90+); 2) myeloid progenitors (MPs; Lin-CD34+CD38+CD123+); and 3) lymphoid progenitors (LPs; Lin-CD34+CD38+CD127+). Each of these populations will be labeled with intensely fluorescent, photostable Qtracker® 525 Qdot® nanocrystals (ThermoFisher), that persist for up to 10 generations. Labeled cells will be used to repopulate the NoC, introducing 5-10×103 HSPC per chip, by individually infusing: 1) HSC; 2) MPs; or 3) LPs into the "input port" of each chip. Flow will then resume.

An LED/CCD camera will be fixed to the chip at the location of each of the specific niches. Chips will be placed in a 37° C. incubator, and these cameras will be used to acquire fluorescence images of each niche at 0.5, 1, 2, 4, 8, 24, 48, and 72 hours, and at 7, 14, 21, and 28 days to quantify the homing and engraftment of the Qtracker® 525-labeled (green) HSC, MPs, and LPs within each specific niche.

To determine whether there is competition between various HSPC for the same niches, HSC, MPs, and LPs will be isolated as above, labeled with Qtracker® 525 (green), Qtracker® 585 (orange), or Qtracker® 655 (red), respectively, and an equal number of each of the 3 cell types (each with a distinct color) will then be infused into the "input port" of the chips. Chips will be placed on the enclosed, heated stage of a Leica TCS LSI confocal microscope, and 3-color images of each niche acquired at 0.5, 1, 2, 4, 8, 24, 48, and 72 hours, and at 7, 14, 21, and 28 days, to evaluate whether competition between the various hematopoietic cells results in alteration in the homing and engraftment patterns seen when each cell type is individually infused into the chips. These three colors can readily be distinguished to identify each cell type.

Example 4

Microfluidic Niche-On-a-Chip Device Fabrication and Niche Construct Biofabrication In Situ.

The microfluidic platform was built using PDMS (10:1 Sylgard 184 silicone elastomer and curing agent respectably, Dow Corning) and a glass slide (VWR, Radnor, PA); both treated and irreversibly bounded with $N_2$ plasma. A convex hemicylindrical microfluidic channel (120 urn height) was fabricated using a modify previously reported standard photolithography technique. Briefly, a primary SU-8 2050 (MicroChem, Westborough, MA) wafer was generated by standard lithography. A primary PDMS device was generated by molding the square channel then the channels were sealed with a 40-µm PDMS membrane. The membrane in the channels was deformed into the channels by a vacuum negative pressure system, SU-8 was placed into them and also spin-coated evenly on a glass slide. Both SU-8 covered surfaces were bind and UV-cured from the top. A final PDMS channel mold was generated for the microfluidic layer.

Following device fabrication, tissue constructs were biofabricated by photopatterning-based cell encapsulation using a hyaluronic acid (HA) and gelatin-based hydrogel. Chambers were filled with Arterial, Sinusoidal, Osteoblast or MSCs cells encapsulated in thiol-modified hyaluronic acid (HA) based hydrogel (ESI-BIO, Alameda, USA), in their respective chamber. A photomask with four equidistant 500 micrometers diameter circles was aligned in the center of the chambers and UV light exposed for crosslinking, followed by PBS and serum free QBSF-60 Stem Cell Medium (Quality Biological, Gaithersburg, MD) washes to remove un-crosslink solution. Using this approach, in the sealed fluidic devices, the hydrogel-based arterial, sinusoidal, MSC, and osteoblast niche constructs were formed and then maintained under circulating flow (10 µL/min).

Platform Operation and Modeling

As illustrated in FIG. 1A-FIG. 1E, devices are designed with a single inlet port (11) in the center of the PDMS part of the device. The connected inlet channel then bifurcates several times, with each of the four resulting channels ending with a circular chamber in which the niche constructs reside. Fluid flow was sufficiently equivalent in each of the 4 arms of the device, resulting in even availability of cells infused through the inlet and recirculated to each of the 4 niche construct sites. This was first visualized by infusion of dyed PBS, where the fluid is shown reaching each chamber approximately at the same time point.

To be more thorough, we created a fluid dynamics computational model of the NOC using ComSol software, in which a simulation of infusing cells into the device was performed by infusing 1000 particles roughly the size of HSPCs. The simulation revealed a heatmap of the fluid flow rates through the virtual device, which indicated that in each parallel region of the device, the simulated fluid flow is approximately equal. Moreover, the location of the groups of infused particles were also predicted to be approximately in parallel locations within the chip at each time point.

3D Niche Construct Characterization On-Chip

Initially, NOC devices containing each of the four niche construct types were maintained under 10 µL/min flow to assess stability and viability of the platform. Devices were maintained for 8 days after which niche-specific biomarkers were assessed through the staining procedures described above. In parallel, viability was determined by LIVE/DEAD staining. Notably, staining was performed directly on chip, and imaging of fluorescent stains was performed using a macro-confocal microscope to take into consideration the 3D nature of the constructs. Arterial constructs stain positive for EphB2. Osteoblastic constructs stain positive for calcium deposits through Alizarin Red staining. Sinusoidal constructs stain positive for EphB4. Mesenchymal constructs stain positive for CD44. These stains were also confirmed on day 3, showing consistency of the platform. In addition, LIVE/DEAD staining shows overwhelmingly high viability, with very few dead cells in all 4 niche construct types. Interestingly in the case of many of the osteoblastic niche constructs, we observed a form of apparent remodeling as the differentiated cells both deposited calcium, but also contracted to some degree into a tighter structure.

HSPC, Lymphoma, and Leukemia Cell Home Predominantly to Specific Niches on NOC Devices For all homing studies, the locations of the four distinct niche constructs were randomized to account for any potential bias of circulating cells based on the device geometry. After 3 days following initiation of NOC device culture, either CD34+ HSPCs, U937 lymphoma cells, or MOLM13 leukemia cells were infused into device during which the micro-peristaltic pump recirculated the media for 5 days. Prior to infusion, the HSPCs, U937, and MOLM13 cells were fluorescently labeled with DiI fluorescent membrane dye to facilitate tracking of the cells via visualization of red fluorescence within the NOC devices. During homing studies, we adapted a micro-camera system, previously employed in other organ-on-a-chip studies, to be compatible with the NOCs. These cameras consisted of an LED light source and a lens that would sit on one side of the NOC, paired with a filter and the camera on the other side of the NOC (FIG. 6). This platform could be employed to take individual snapshots of the constructs, or to capture videos in which one could actually observe labeled cells traveling through the recirculating system and either engrafting into the constructs, or passing by or transiently attaching and releasing from the constructs.

We could also capture images both in the fluorescent channel and by light microscopy, and superimpose these images to better appreciate the locations over time in which fluorescently-labeled cells were at any given time. With these superimposed images, we also employed a methodology through ImageJ software to quantify the presence of the infused cells at each construct site. Briefly, following biofabrication of each niche construct, a digital mask was determined that corresponded with the circumference of that particular construct, defining the region of the construct in which engrafted cells could be detected. Next the fluorescent and light microscopy superimposed image was created at each subsequent time point during the study. The digital mask from the initial timepoint was then applied to these overlays, after which the cells outside the mask were erased, and the red cells were turned to white. Lastly, black/white thresholding was employed to turn the white regions into black, and a script was used to break large features into cell-sized objects for quantification.

Interestingly, it became clear that the 3 infused cell types—CD34+ HSPCs, U937 lymphoma cells, and MOLM13 leukemia cells—did indeed show preference for homing to and engrafting to particular niche constructs. The CD34+ HSPCs engrafted to some degree in mesenchymal and sinusoidal niche constructs, and while not statistically significant, showed a clear trend of preferential engraftment in the osteoblastic niche constructs. Few CD34+ HSCs homed to the arterial niche constructs, and even appeared to initially engraft, but then release. The U937 lymphoma cells also engrafted some in the mesenchymal and sinusoidal niche constructs, more so in the osteoblastic niche constructs, but by far engrafted the most in the arterial niche constructs. Lastly, the MOLM13 leukemia cells, displayed homing behavior more like that of the HSPCs, engrafted some in the mesenchymal and sinusoidal niche constructs, most in the osteoblastic niche constructs, followed by the arterial niche constructs.

The foregoing is illustrative of the present invention, and is not to be construed as limiting thereof. The invention is defined by the following claims, with equivalents of the claims to be included therein.

What is claimed is:

1. An in vitro construct useful as a model for a hematopoietic microenvironment comprising:
   a microfluidic device having multiple chambers; and
   three or four populations of cells selected from: 1) mesenchymal cells; 2) osteoblasts; 3) arterial endothelium; and 4) sinusoidal endothelium,
   wherein each of said populations of cells are provided in a separate chamber of the microfluidic device.

2. The construct of claim 1, wherein the mesenchymal cells, osteoblasts, arterial endothelium, and/or sinusoidal endothelium cells are adult human bone marrow mononuclear cells.

3. The construct of claim 1, wherein the construct comprises all four of the populations of cells.

4. The construct of claim 1, wherein the populations of cells share a common media.

5. The construct of claim 1, wherein the populations of cells are provided in a hydrogel carrier.

6. The construct of claim 1, wherein said populations are patterned to form a circular construct within the chambers of the microfluidic device.

7. The construct of claim 1, wherein said populations are patterned to form a channel that allows fluid flow around or through each of the populations of cells in the chambers.

8. The construct of claim 1, wherein test cells may be infused into the construct and through each of the chambers.

9. The construct of claim 8, wherein the test cells comprise malignant blood cells or circulating tumor cells from a patient.

10. The construct of claim 1, wherein said microfluidic device comprises a common inlet in fluid communication with each of the chambers.

11. The construct of claim 1, wherein said chambers are connected by microchannels.

12. The construct of claim 1, wherein said microfluidic device comprises an LED and/or CCD detector positioned to allow images of labeled cells in contact with the multiple chambers to be imaged and/or quantified in real time.

13. The construct of claim 1, wherein the populations of cells of the microfluidic device are from the same subject.

14. The construct of claim 1, wherein the microfluidic device comprises:
   (i) a housing,
   (ii) one or more fluid inlets in the housing, said chambers in fluid communication with the one or more of the fluid inlets by way of one or more fluid channels in the housing, and
   (iii) one or more fluid outlets in the housing in fluid communication with the chambers by way of the fluid channels.

15. A system comprising the in vitro construct of claim 1, a pump, a media reservoir, and associated tubing.

16. The system of claim 15, wherein the system is a closed, recirculating system.

17. The construct of claim 1, wherein each of the multiple chambers comprises walls, and the walls of the chambers are impermeable to the cells.

18. The construct of claim 5, wherein the hydrogel carrier is crosslinked.

19. The construct of claim 10, wherein the common inlet is equidistant to each of said chambers.

20. A method of making the in vitro construct of claim 1, comprising:
   providing a microfluidic device or a layer thereof having multiple chambers; and
   depositing into the chambers three or more populations of cells selected from: 1) mesenchymal cells; 2) osteoblasts; 3) arterial endothelium; and 4) sinusoidal endothelium,
   wherein each of said populations of cells are deposited into a separate chamber of the microfluidic device.

21. The method of claim 20, wherein said depositing is carried out by bioprinting a composition comprising one of the populations of cells into a chamber of the microfluidic device.

22. The method of claim 21, wherein said composition comprises a hydrogel.

23. The method of claim 20, wherein said depositing is patterned depositing.

24. The method of claim 20, wherein said populations of cells are provided in a hydrogel carrier, and the method further comprises patterned crosslinking of the hydrogel carrier in the chambers.

25. The method of claim 23, wherein said depositing and/or crosslinking is patterned to form one or more channels that allows fluid flow around or through each of the populations of cells.

26. The method of claim 25, wherein said method further comprises endothelializing some or all of the channels.

27. A method of detecting a cellular response to test cells and/or active agent(s) in a hematopoietic microenvironment, comprising:
   (a) providing a microfluidic device of claim 1;
   (b) optionally circulating a medium through the chambers of the microfluidic device;
   (c) administering the test cells and/or active agent(s) to the populations of cells in the device, or irradiating the populations of cells of the device with ionizing radiation (IR); and
   (d) detecting a cellular response to the test cells and/or active agent(s), or IR.

28. The method of claim 27, wherein detecting the cellular response comprises comparing the response to a response (or lack of a response) observed when active agent(s) are administered with cells.

29. The method of claim 27, wherein the circulating is carried out in some or all of the chambers at a physiological flow rate.

30. The method of claim 27, wherein the administering is carried out with cells that are labeled and wherein the detecting is carried out by detecting a signal thereof.

31. The method of claim 27, wherein the administering is carried out with test cells comprising malignant blood cells or circulating tumor cells from a patient.

32. The method of claim 27, wherein the administering is carried out with malignant HSPC test cells.

33. The method of claim 27, wherein the administering is carried out with normal (non-cancerous) test cells.

34. The method of claim 31, wherein the test cells are from the same subject as the populations of cells of the microfluidic device.

35. The method of claim 27, wherein administering comprises administering cells and the cells are labeled with a detectable group and/or a genetic barcode.

* * * * *

UNITED STATES PATENT AND TRADEMARK OFFICE
CERTIFICATE OF CORRECTION

| | |
|---|---|
| PATENT NO. | : 11,826,757 B2 |
| APPLICATION NO. | : 16/635703 |
| DATED | : November 28, 2023 |
| INVENTOR(S) | : Porada et al. |

It is certified that error appears in the above-identified patent and that said Letters Patent is hereby corrected as shown below:

In the Specification

Column 5, Line 15: Please correct "off 10%" to read --of ±10%--

Column 17, Line 23: Please correct "120 urn" to read --120 µm--

Signed and Sealed this
Thirteenth Day of February, 2024

Katherine Kelly Vidal
*Director of the United States Patent and Trademark Office*